United States Patent
Irlam et al.

(10) Patent No.: US 8,265,900 B2
(45) Date of Patent: Sep. 11, 2012

(54) MOTION ANALYSIS DEVICE FOR SPORTS

(75) Inventors: James Christopher Irlam, Staines (GB); Lisa Jane Irlam, Staines (GB)

(73) Assignee: Swimovate Limited, Wraysbury, Staines, Middlesex (GB)

( * ) Notice: Subject to any disclaimer, the term of this patent is extended or adjusted under 35 U.S.C. 154(b) by 182 days.

(21) Appl. No.: 12/642,830

(22) Filed: Dec. 20, 2009

(65) Prior Publication Data
US 2010/0204952 A1    Aug. 12, 2010

Related U.S. Application Data

(60) Provisional application No. 61/203,845, filed on Dec. 30, 2008.

(51) Int. Cl.
*G01C 22/00* (2006.01)
*G06F 11/00* (2006.01)

(52) U.S. Cl. ......... 702/160; 702/176; 702/188; 702/189

(58) Field of Classification Search .................. 702/160, 702/176–188, 121–123
See application file for complete search history.

(56) References Cited

U.S. PATENT DOCUMENTS

| | | | |
|---|---|---|---|
| 5,125,010 A | 6/1992 | Lee | |
| 5,760,691 A | 6/1998 | Egli | |
| 5,864,518 A | 1/1999 | Geiser | |
| 7,345,958 B1 | 3/2008 | Kneafsey | |
| 2003/0138763 A1* | 7/2003 | Roncalez et al. | 434/254 |
| 2004/0020856 A1 | 2/2004 | Wong et al. | |
| 2004/0102931 A1* | 5/2004 | Ellis et al. | 702/188 |
| 2005/0186542 A1 | 8/2005 | Roncalez | |
| 2007/0054778 A1 | 3/2007 | Blanarovich et al. | |
| 2008/0018532 A1* | 1/2008 | Mackintosh et al. | 342/357.12 |
| 2008/0288200 A1 | 11/2008 | Noble | |
| 2010/0210975 A1 | 8/2010 | Anthony, III et al. | |

FOREIGN PATENT DOCUMENTS

| | | |
|---|---|---|
| EP | 1992389 | 11/2008 |
| GB | 2176036 | 12/1986 |
| WO | 00/36520 | 6/2000 |
| WO | 2010090867 | 8/2010 |

* cited by examiner

*Primary Examiner* — Phuong Huynh
(74) *Attorney, Agent, or Firm* — Price Heneveld LLP

(57) ABSTRACT

There is described a portable wrist worn device for determining information about the movement of a human body when swimming. The device comprises a waterproof housing containing: an accelerometer operable to generate an acceleration signal; a processor operable to process the acceleration signal so as to generate one or more metrics relating to the movement of the human body; and a means for feedback of the one or more metrics to the user. The accelerometer may be operable to generate an acceleration signal along an axis parallel to the proximo-distal axis of the user's arm in use and/or the accelerometer may be operable to generate an acceleration signal along an axis parallel to the dorsal-palmar axis of the user's hand in use. The device may also be used in sports other than swimming.

14 Claims, 5 Drawing Sheets

MOTION ANALYSIS DEVICE FOR SPORTS

CROSS REFERENCE TO RELATED APPLICATIONS

This application claims the benefit of provisional patent application Ser. No. 61/150,769, filed 2009 Feb. 2 by the present inventors.

FEDERALLY SPONSORED RESEARCH

Not applicable

SEQUENCE LISTING OR PROGRAM

Not applicable

BACKGROUND

1. Field

The present invention relates to a portable wrist worn device for determining information about the movement of a human body when swimming. The device may also be used in sports other than swimming.

2. Prior Art

There is a requirement to study the motion undertaken by an object or body. In particular this is of interest in the field of sport and athletic endeavours. Athletes need to know how fast and how much distance they have covered during exercise and how this compares with other athletes or past performances. Such a system should be relatively small in size and lightweight, so as not to hinder movement, and be of low cost, low power and high accuracy. It requires the means to process and relay motion data parameters back to the user during or after exercise.

Motion sensing devices are common in the sports of running and cycling and use various techniques such as GPS, mechanical switches, piezoelectric devices and accelerometers to obtain speed and distance information. There is a requirement by athletes engaged in other sports, such as swimming, to obtain speed and distance information.

All swimmers are used to counting laps and aware of the frustration when the total is forgotten or miscounted. There are several devices that allow a swimmer to manually count laps by pressing a button or turning a dial after each lap. U.S. Pat. No. 7,345,958 describes a wrist worn device that shows a swimmers lap count. The swimmer presses a button on the device at the end of each lap to increment the counter. However, this is awkward to use in practice and a swimmer can also forget to press the button to increment the lap. An automatic lap counting system would be much more desirable. A watch was produced by Speedo based on U.S. Pat. No. 5,864,518. This used the conductivity of the water to detect if the watch was immersed. Hence this gave stroke counting information but only for strokes where the arm comes out of the water (back stroke, front crawl and butterfly). However, the operation depended on the electrodes being kept clean and the product was discontinued after a short time. The method described in this document does not rely on conduction through water, has no external electrodes to keep clean and will also work with breaststroke, the most popular of the recreational swim strokes. Although the Speedo device calculated a number of metrics, it did not show a numerical count of a swimmer's laps. The number of laps swam is probably the most useful metric a swimmer can have.

U.S. Pat. No. 5,125,010 describes an automatic lap counting system with radio communication including a wrist worn transmitter and poolside receiver. By employing radio frequency, the lap counting system increments a lap count each time the distance between the receiver and the transmitter becomes smaller than the communication range. Placing a separate receiver on the poolside is inconvenient and undesirable in many public swimming pools and adds significantly to the price of manufacturing the product. There is a need to create a device that automatically counts and relays this information to a swimmer that consists of a single, low cost device worn on the swimmer's body.

MEMS accelerometers are small, sensitive, low power and low cost so are suitable for building into portable devices. US patent 2005/0186542 describes a device worn on the swimmer's back that uses accelerometers to work out lap and stroke data from the change in the acceleration signal on the longitudinal axis of the human body. In practice a device worn on the back has limitations in that it is awkward to position and also requires an additional display or feedback device to be used to relay information back to the swimmer. Additionally this device requires calibration for each individual swimmer which is undesirable to the user. US patent 2008/0018532 describes an invention incorporating accelerometers and a GPS receiver as a data acquisition system for swimmers. GPS receivers have many disadvantages. They are high power, high cost and have difficulty attaining signals indoors. The RF signal associated with GPS is heavily attenuated when immersed in water. Even outdoors they may not be accurate enough to detect changes in laps.

Prior art fails to show a low cost, discrete device that automatically calculates and displays accurate lap counts, stroke counts, speed and distance data for swimmers, for all strokes, that can be worn on the wrist.

BRIEF SUMMARY OF THE INVENTION

According to a first aspect of the present invention, there is provided a wrist worn device for determining information about the movement of a human body when swimming. The device comprises a waterproof housing containing: an accelerometer operable to generate an acceleration signal; a processor operable to process the acceleration signal so as to generate one or more metrics relating to the movement of the human body; and a means for feedback of the one or more metrics to the user.

In one embodiment, there is provided a wrist worn device for determining information about the movement of a human body when swimming. The device comprises a waterproof housing containing: one or more accelerometers to generate acceleration signals; a processor capable of generating a plurality of metrics from the acceleration signals; and a means for feedback to the user.

The information about the movement may consist of lap or stroke counts. The information about the movement may be further processed to obtain speed and distance metrics. Additional metrics such as calories or efficiency may be calculated. The device may comprise two accelerometers arranged such that one axis is aligned longitudinally along the proximo-distal axis and one axis arranged perpendicular along the dorsal-palmar axis. The means for user feedback may be a visual display.

Thus, the present invention provides a portable wrist worn device incorporating one or more accelerometers that give athletes engaged in repetitive movement feedback about their performance. The device can be built into a wearable device incorporating a display, so data can be viewed by the athlete during and after training sessions. One embodiment of the invention is a wearable computer for swimming that automatically counts strokes and laps. A host of training information can be derived from these parameters including distance, speed, efficiency, energy expenditure and their statistics. Such devices would allow swimmers to concentrate on their technique without having to keep a mental tally of laps or strokes and also provide much more insight into swimming performance.

Other preferred features of the present invention are set out in the appended claims.

BRIEF DESCRIPTION OF THE DRAWINGS

A more complete understanding of the present invention and at least some features and advantages thereof may be acquired by referring to the following description and the accompanying drawings. It will be appreciated that for simplicity and clarity of illustration, elements illustrated in the Figures have not necessarily been drawn to scale.

DETAILED DESCRIPTION OF THE DRAWINGS

An embodiment of the invention is described below that utilizes one two-dimensional accelerometer to measure and display the motion parameters of a swimmer in a device worn on the swimmer's wrist, it is to be understood that other embodiments may be utilized and structural and functional modifications may be made without departing from the scope of the present invention. The embodiment may be incorporated into a sports watch. The invention is not restricted to a sports watch or particular sporting activity and can be utilized for sports other than swimming such as rowing or kayaking. It can also be used in other fields where the motion of a body is analyzed such as in virtual reality or games consoles.

MEMS accelerometers are small size, low cost, low power and readily available so are suitable for a discrete wrist watch based design, however difficulties exist in their use. Accelerometers measure the sum of all the components of acceleration acting on them, both static and dynamic. Static acceleration is that experienced when the device is stationary and in practice we can equate this to the acceleration due to gravity experienced by the accelerometer. The static acceleration detected depends on the orientation of the accelerometer with respect to the vertical axis. When the accelerometer is tilted with respect to this axis, the amount of static acceleration detected by the accelerometer changes. Dynamic acceleration is produced by the motion of the body. This may be along a certain axis of motion, rotational or a combination of the two. In respect to a swimmer's arm, static acceleration due to gravity, dynamic acceleration in the direction of swimming and also the centrifugal acceleration of the arm around the shoulder and the tangential component of this, are all experienced. These are cumulatively sensed and outputted by the accelerometer. It is also well known that an accelerometer's output drifts over time due to temperature and environmental changes. We propose a method of motion analysis that takes these limitations into account and is unaffected by any drift in signal over time.

Figure 1:
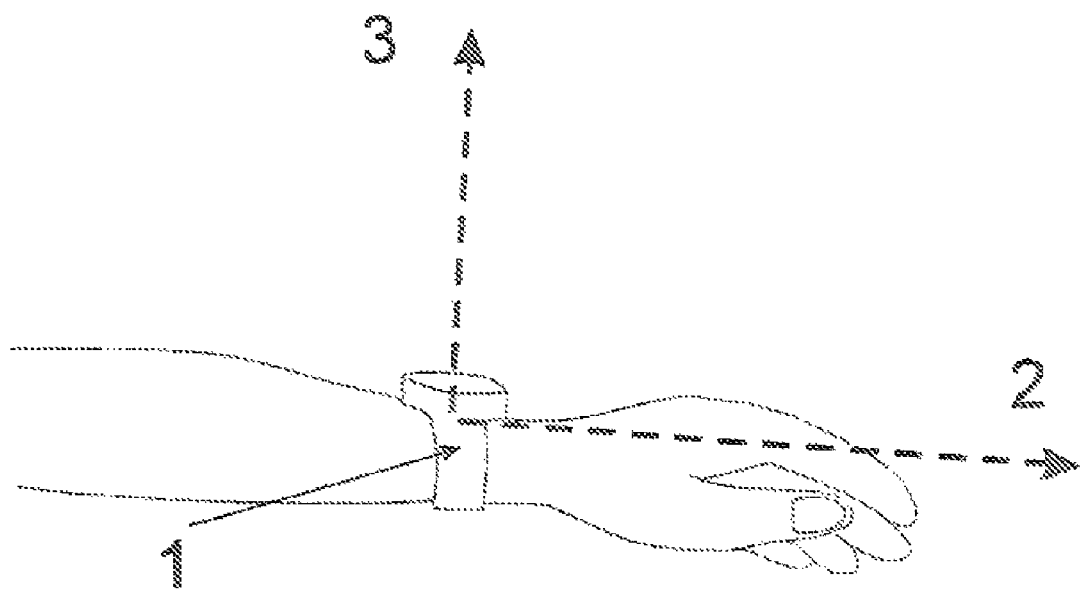
FIG. 1 illustrates a preferred embodiment on an athlete's arm showing the axes of the accelerometer.

Referring to FIG. 1, a preferred embodiment consists of a device (1) containing one two axis accelerometer positioned on the wrist of a swimmer. The accelerometer is arranged such that the measuring axes are offset to each other at angles of 90 degrees. One axis is arranged parallel to the swimmer's arm along the proximo-distal axis, y (2) and the other perpendicular, along the dorsal-palmar axis, z (3). Other spatial arrangements of accelerometer may be used including multiple single devices or one three axis device commonly available from manufacturers such as Analog Devices or Freescale Semiconductor. In a preferred embodiment the accelerometers are part of a MEMS three axis accelerometer package.

Figure 2:
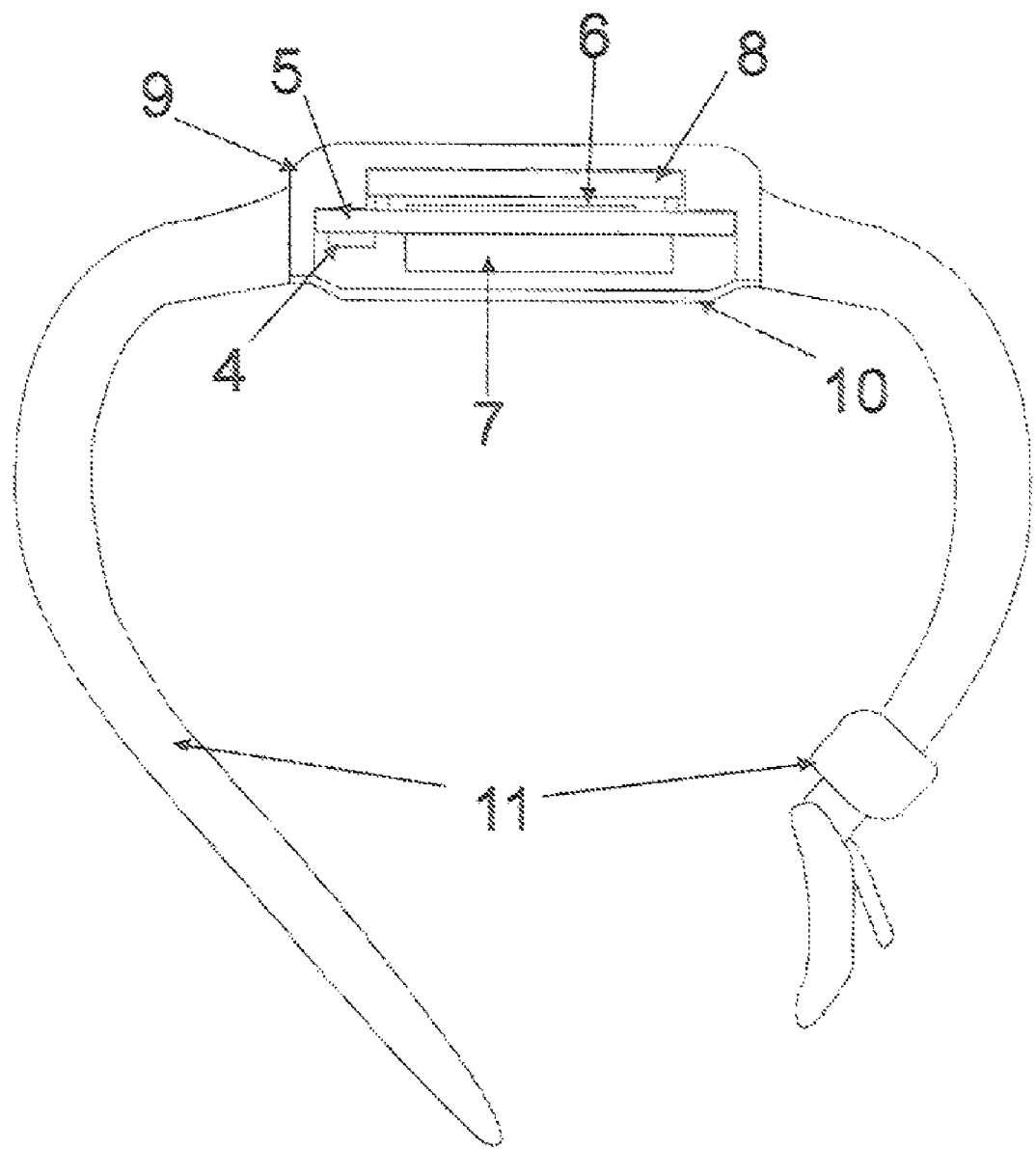
FIG. 2 illustrates the cross section through an embodiment of the disclosure illustrating the internal layout.

FIG. 2 shows the main layout features of the electronics. The accelerometer (4) is mounted on a printed circuit board (5). The printed circuit board is connected to a microcontroller (6), battery (7) and LCD display (8) and secured in a waterproof case (9) by a back plate (10) and fastened to the user by an adjustable strap (11). Those skilled in the art will recognize that suitable microcontrollers and batteries are available from a wide range of manufacturers.

Figure 3:
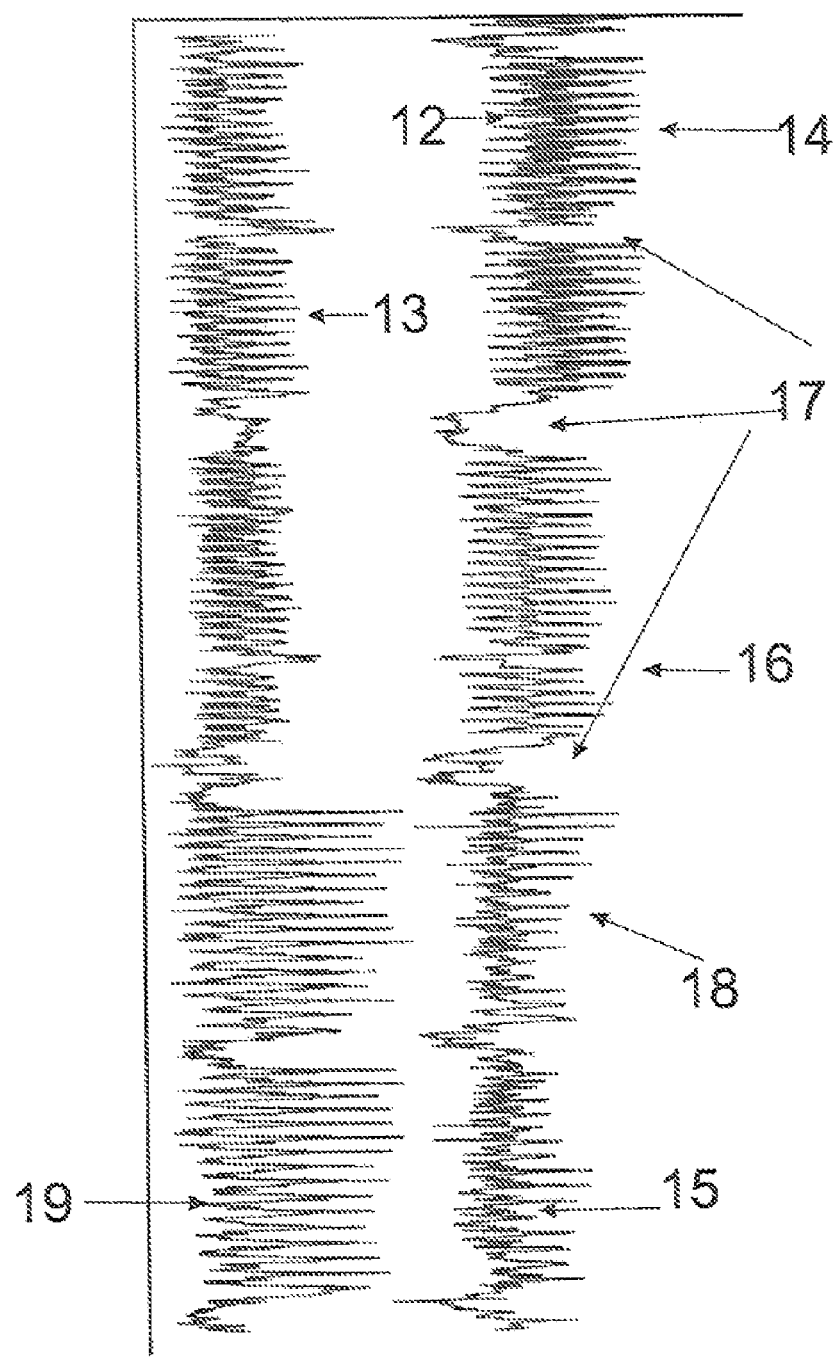
FIG. 3 shows accelerometer data along the y and z axes for various swimming strokes.

The movements experienced by a human arm when swimming laps in a pool are repetitive in nature. The data outputted from the accelerometer is shown in FIG. 3. The upper trace (12) displays the accelerometer output from the y axis and the lower trace (13) shows the output from the z axis for a swimmer. It can be seen that when a swimmer is swimming, a regular pattern can be detected relating to the individual strokes the swimmer makes. The exact nature of the signal differs for each stroke in form including amplitude and frequency, this is shown for (14) Frontcrawl, (15) Backcrawl and (16) Breaststroke. When the swimmer turns and changes lap, a gap in the regular pattern occurs (17). When the swimmer stops swimming altogether the output becomes irregular (18).

It can be seen that the signal from the accelerometer along the proximo-distal axis of the wrist (y) displays regular data for breaststroke (16) and frontcrawl (14) whereas the signal for backstroke (15) is less regular. Looking at the dorsal-palmar axis (x), the output for backstroke (19) is more regular in this plane. Hence more than one axis is required to obtain stroke information for the major strokes.

Figure 4:
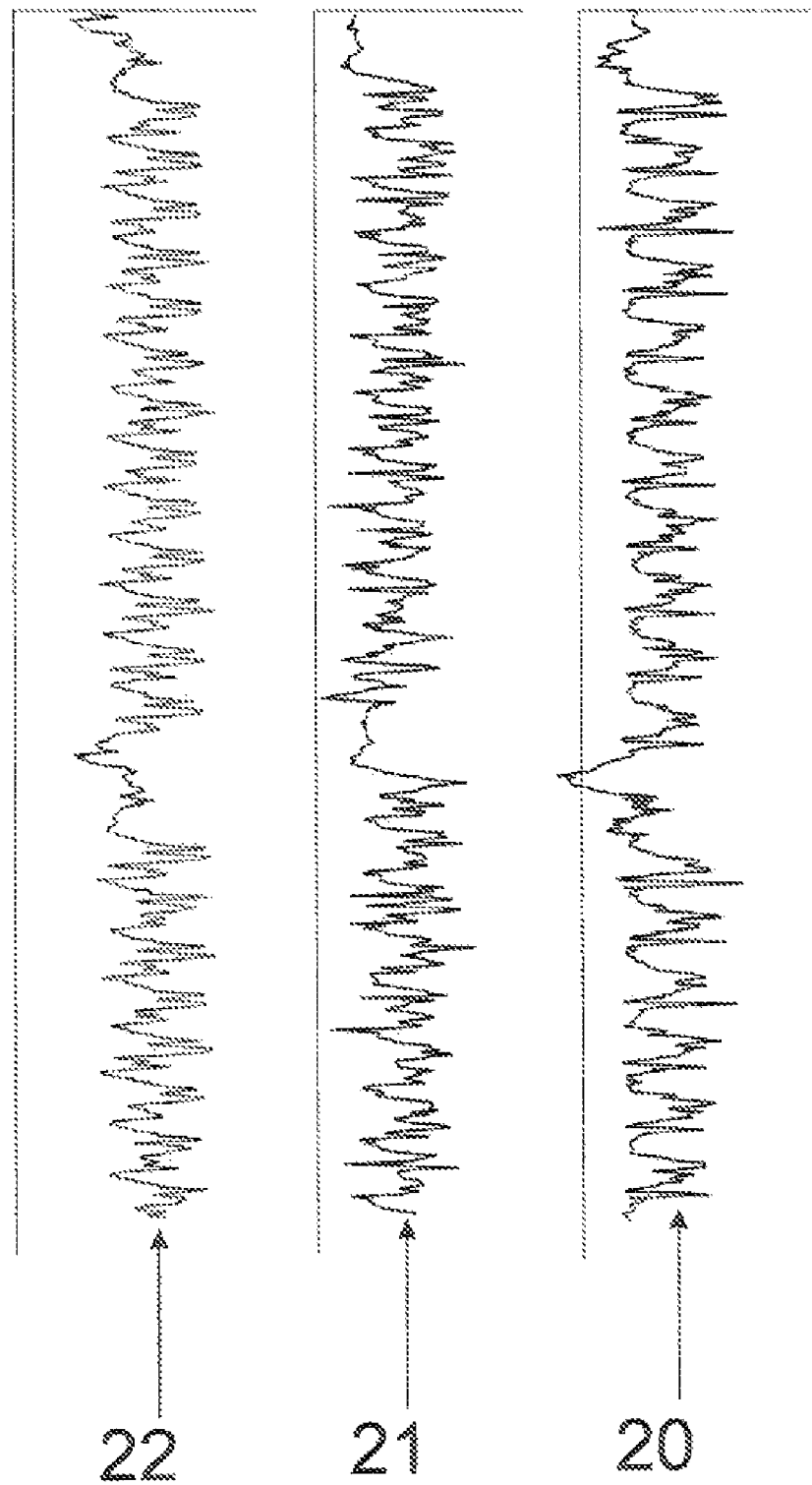
FIG. 4 shows accelerometer data for three different swimmers along the y axis.

The signal when swimming also differs between swimmers, especially those of differing abilities. FIG. 4 shows the accelerometer output for the y axis for 3 different swimmers (20), (21) and (22) all swimming frontcrawl.

An ideal algorithm will process lap and stroke data for all major strokes and with all abilities of swimmer, without calibration, it must take into account the data from multiple axes.

The accelerometer produces data at a faster rate than required. A fixed moving average is used as a simple anti-alias filter and then the data is down-sampled to the desired sample rate. The detection algorithm uses the data at a regular rate. The rate chosen ensures that many samples are available per stroke cycle.

The algorithm works in a number of stages. The first stage extracts the underlying trend from the complex noise-like signal. To do this raw samples are smoothed with an adaptive multiple-pass moving average. The length of the moving average is adjusted during operation to ensure that the total signal excursion (max-min) is within a defined range. Smoothing with a fixed length moving average was unsatisfactory because the length of average required for a slow signal causes faster signals to be smoothed too much and therefore removes valuable detail. The adaptive moving average produces trend data that has relatively constant amplitude for any speed of signal.

A moving average is used because it can be implemented on a microcontroller in a few simple instructions i.e. it is very low overhead. However, a single pass moving average has a straight-line step response that does not smooth data very well. Multiple-pass moving averages have smoothly varying step responses but can still be made to run fast on small processors such as the one used in the embodiment.

The position and values of maxima and minima in the smoothed data are found by a simple peak detection routine. The values of the maxima and minima are averaged to determine the mid-level value of the signal. Maxima below this level are rejected as they are not considered true maxima. If the accelerometer's signal drifts due to environmental changes the difference between maxima and minima will be unaffected even if the absolute values may be offset due to drift.

The time delays between consecutive valid maxima are stored in a small queue. As each maxima is found the stored delays are compared to find the total variation. When this variation is small it means that the maxima are occurring at regular intervals and this is consistent with the arm moving during swimming. When the end of a lap is reached, or the user stops swimming there will be a much larger gap between the maxima and this increase in variation can be detected.

Parameters used during the algorithm (e.g. the length of the moving average and number of multiple passes) were determined empirically using data from many swimmers. Hence by counting the number of large gaps between maxima we obtain the number of laps swum and by counting the number of small gaps between these, the strokes per lap are obtained.

As previously explained, the major strokes, apart from backstroke, have their most regular accelerometer signals on the y axis but backstroke has a more regular signal on the z axis. If the y axis is used to determine strokes during backstroke, several strokes are missed as the maxima and minima relating to each stroke are not large enough to be detected by the algorithm. However if we apply the algorithm to the z axis, the stroke count for backstroke is accurate. Similarly using the z axis alone results in inaccurate stroke counts for the other strokes. Hence the algorithm needs to be applied to both axes. If the stroke count for one axis is greater than the other over a lap, the data from this axis is used for the calculations and the other rejected. This is similarly applied to lap counting. If the lap count on one axis is greater than the other then data from this axis is picked and the other rejected. If a device is required for use with Frontcrawl and breaststroke only, then a single accelerometer with the axis of measurement aligned along the proximo-distal axis can be used. Additionally further accuracy may be obtained by the addition one or more accelerometers with the axis of measurement in largely different planes. The algorithm can be applied to all signals as described above.

Figure 5:
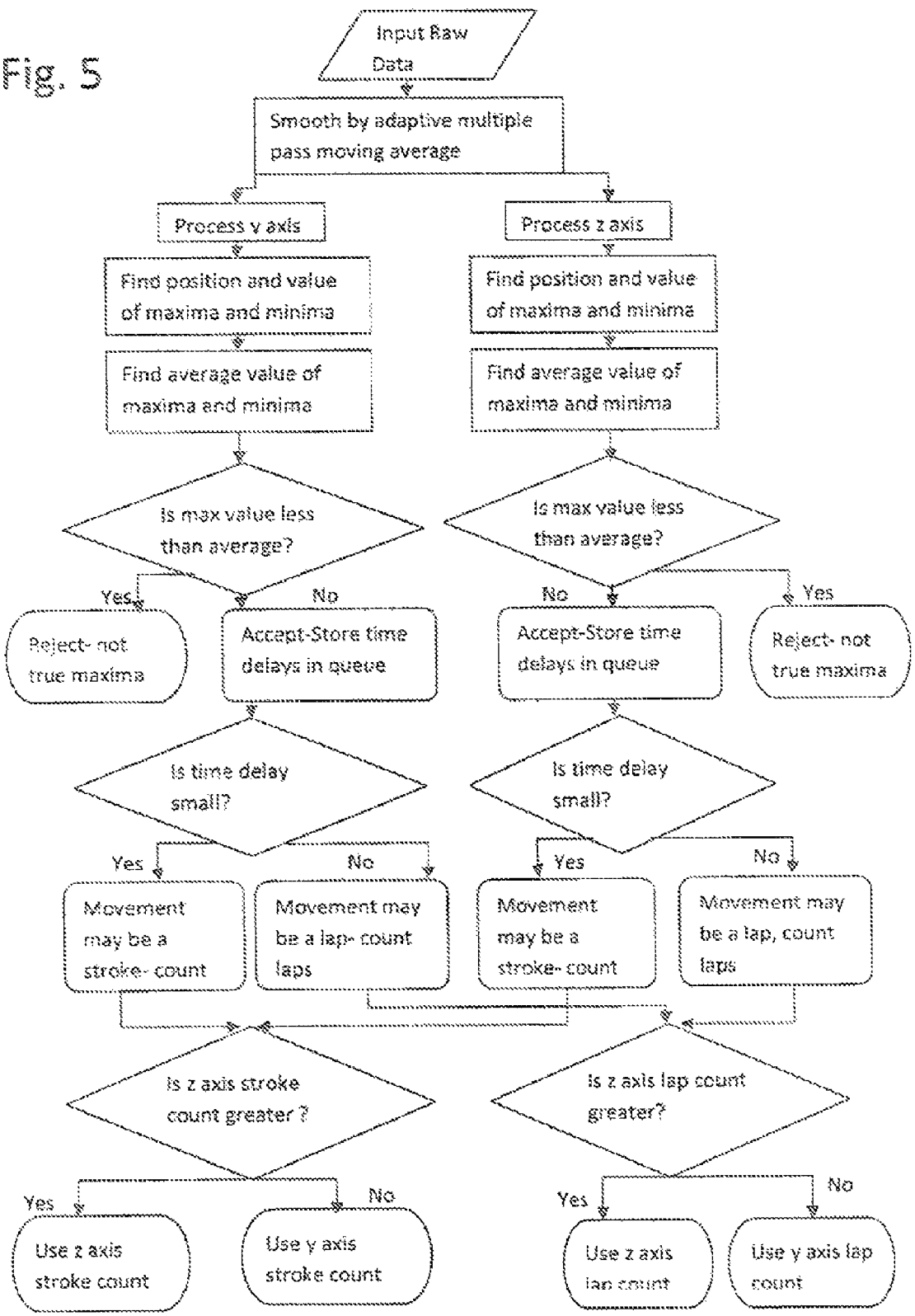
FIG. 5 shows a flowchart describing the operation of the stroke and lap counting algorithm.

FIG. 5 shows a flowchart depicting the methods and decisions used by the stroke and lap counting algorithm.

Once the number of laps is known, speed can be calculated by simple arithmetic knowing the length of lap and time taken per lap. Likewise the distance traveled is the number of laps multiplied by the length of the pool. The calories a swimmer expends when exercising can be approximated by a function of weight and speed. The preferred embodiment allows the user to program in body weight before exercising so calories can be calculated and displayed. The method of calorie calculation is not limited to this method. Those skilled in the art will be familiar with other methods that may be more accurate and may require additional information such as sex, height or body mass index.

Several coaches and trainers recognize the importance of counting strokes per lap. It is generally believed that to improve efficiency and reduce effort the number of strokes per lap should be minimized. A measure of a swimmer's efficiency can be calculated by adding the number of strokes to the time taken per lap. This is commonly known as "Swim Golf" score. Expert swimmers have low counts whereas poorer swimmers have higher counts. The swimmer should try to reduce this number over a period of time.

The preferred embodiment provides comprehensive information about the user's swim session by calculating and displaying lap count, average stroke per lap count, time elapsed, speed, distance, calories burnt and a swimming efficiency index, pace and cadence. In a further embodiment, a preset distance or lap count can be programmed into the device and an alarm set that warns the swimmer when he is approaching the specified parameter. The alarm could be vibrational, audible or visual in nature. Additionally a specified pace, cadence or speed can be preset, when a swimmer deviates from this, an alarm is activated so the device warns the swimmer to change their stroke accordingly.

Further sensors, such as, but not limited to, ones that detect heart rate or body temperature, can be added to the embodiment to give extra information to the swimmer about the quality of the swimming session.

The invention claimed is:

1. A wrist worn device for determining information about the movement of a human body when swimming, the device comprising a waterproof housing containing:
   at least one accelerometer operable to generate both a first acceleration signal along an axis parallel to the proximo-distal axis of the user's arm in use and a second acceleration signal along an axis parallel to the dorsal-palmar axis of the user's arm in use;
   a processor operable to process the first acceleration signal and to thereby generate a first value of a swimming metric relating to movement of the human body and operable to process the second acceleration signal and to thereby generate a second value of said swimming metric, the processor further being operable to compare the first and second values of said swimming metric and to select the greater of the two as a selected value;
   a means for feedback of the selected value of said swimming metric to the user; and
   wherein said swimming metric comprises one swimming metric chosen from the group consisting of a lap count and a stroke count.

2. The device of claim 1, wherein the at least one accelerometer consists of one two-dimensional accelerometer.

3. The device of claim 1, wherein the at least one accelerometer consists of one three-dimensional accelerometer.

4. The device of claim 1, wherein the at least one accelerometer consists of two one-dimensional accelerometers spatially arranged such that one generates the first acceleration signal along the axis parallel to the proximo-distal axis of the user's arm and the other generates the second acceleration signal along the axis parallel to the dorsal palmar axis of the user's hand in use, the two accelerometer axes being mutually perpendicular.

5. The device of claim 1, wherein said swimming metric comprises a lap count, and wherein the processor is further operable to process the first acceleration signal and to thereby generate a first value of a second swimming metric and to process the second acceleration signal and to thereby generate a second value of the second swimming metric, the processor further being operable to compare the first and second values of the second swimming metric and to select the greater of the two as a selected value, wherein the means for feedback provides both the selected value of the swimming metric and selected value of the second swimming metric to the user; and wherein the second swimming metric comprises the stroke count.

6. The device of claim 5, wherein the processor is further operable to use the selected value of the lap count and the selected value of the stroke count to calculate the number of strokes per lap.

7. The device of claim 1, wherein said swimming metric comprises a lap count, and wherein the processor is further operable to use the selected value of the lap count to calculate at least one parameter chosen from the group consisting of speed, distance and calories burnt, relating to the movement of the human body.

8. The device of claim 1, wherein the means for feedback is a visual display.

9. The device of claim 1, wherein the processing algorithm comprises:
- a moving average algorithm for smoothing a raw acceleration signals;
- a peak detection algorithm for detecting maxima and minima in the smoothed acceleration signal; and
- a time delay calculation algorithm for calculating the time delays between consecutive detected maxima.

10. The device of claim 1 further comprising an alarm operable to warn the user when a preset value of the swimming metric is reached.

11. The device of claim 1 further comprising a heart rate sensor for sensing the heart rate of the user.

12. The device of claim 1 further comprising a temperature sensor for sensing the body temperature of the user.

13. The device of claim 1, wherein the device comprises a watch.

14. A method of determining information about the movement of a human body when swimming, the method comprising the steps of:
- generating a first acceleration signal along an axis parallel to the proximo-distal axis of a swimmer's arm;
- generating a second acceleration signal along an axis parallel to the dorsal-palmar axis of the swimmer's arm;
- processing the first acceleration signal and thereby generating a first value of a swimming metric relating to the movement of the human body;
- processing the second acceleration signal and thereby generating a second value of said swimming metric;
- comparing the first and second values of said swimming metric and selecting the greater of the two as a selected value; and
- outputting the selected value of said swimming metric to the user;
- wherein said swimming metric comprises one swimming metric chosen from the group consisting of a lap count and a stroke count.

* * * * *